United States Patent
Nalesnik

(10) Patent No.: US 6,566,311 B1
(45) Date of Patent: May 20, 2003

(54) 1,3,4-OXADIAZOLE ADDITIVES FOR LUBRICANTS

(75) Inventor: Theodore E. Nalesnik, Hopewell Junction, NY (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 11 days.

(21) Appl. No.: 09/996,775

(22) Filed: Nov. 30, 2001

(51) Int. Cl.⁷ ............................................. C10M 133/48
(52) U.S. Cl. ..................................................... 508/278
(58) Field of Search ......................................... 508/278

(56) References Cited

U.S. PATENT DOCUMENTS

| | | | |
|---|---|---|---|
| 3,293,181 A | 12/1966 | Stuart | 252/32.7 |
| 3,396,109 A | 8/1968 | Butler et al. | 252/32.7 |
| 3,397,145 A | 8/1968 | Cyba | 252/32.7 |
| 3,442,804 A | 5/1969 | Suer et al. | 252/32.7 |
| 3,637,499 A | 1/1972 | Pollak | 252/32.7 |
| 5,084,195 A | 1/1992 | Camenzind et al. | 252/47.5 |
| 5,300,243 A | 4/1994 | Camenzind et al. | 252/47.5 |
| 5,498,809 A | 3/1996 | Emert et al. | 585/13 |
| 5,512,190 A | 4/1996 | Anderson et al. | 252/47 |
| 5,514,189 A | 5/1996 | Farng et al. | 44/383 |
| 6,458,750 B1 * | 10/2002 | Dardin et al. | |

* cited by examiner

Primary Examiner—Jerry D. Johnson
(74) Attorney, Agent, or Firm—Daniel Reitenbach

(57) ABSTRACT

Disclosed herein is a composition comprising:
  (A) a lubricant, and
  (B) at least one 1,3,4-oxadiazole compound of the formula:

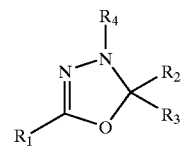

wherein
  wherein $R_1$ is selected from the group consisting of hydrogen, linear or branched alkyl, alkenyl, alkaryl, aryl, alkyl ether, and alkyl ester;
  $R_2$, $R_3$, and $R_4$ are independently selected from the group consisting of hydrogen, linear or branched alkyl, alkenyl, alkaryl, and aryl; and
  any alkyl moiety can optionally contain within it oxygen ether, ester, or amide groups.

20 Claims, No Drawings

1,3,4-OXADIAZOLE ADDITIVES FOR LUBRICANTS

BACKGROUND OF THE INVENTION

1. Field of the Invention

This invention is related to lubricants, especially lubricating oils, and, more particularly, to a class of ashless and non-phosphorus, non-sulfur-containing anti-wear, anti-fatigue, and extreme pressure additives derived from 1,3,4-oxadiazoles.

2. Description of Related Art

In developing lubricating oils, there have been many attempts to provide additives that impart anti-fatigue, anti-wear, and extreme pressure properties thereto. Zinc dialkyldithiophosphates (ZDDP) have been used in formulated oils as anti-wear additives for more than 50 years. However, zinc dialkyldithiophosphates give rise to ash, which contributes to particulate matter in automotive exhaust emissions, and regulatory agencies are seeking to reduce emissions of zinc into the environment. In addition, phosphorus, also a component of ZDDP, is suspected of limiting the service life of the catalytic converters that are used on cars to reduce pollution. It is important to limit the particulate matter and pollution formed during engine use for toxicological and environmental reasons, but it is also important to maintain undiminished the anti-wear properties of the lubricating oil.

In view of the aforementioned shortcomings of the known zinc and phosphorus-containing additives, efforts have been made to provide lubricating oil additives that contain neither zinc nor phosphorus or, at least, contain them in substantially reduced amounts.

Illustrative of non-zinc, i.e., ashless, non-phosphorus-containing lubricating oil additives are the reaction products of 2,5-dimercapto-1,3,4-thiadiazoles and unsaturated mono-, di-, and tri-glycerides disclosed in U.S. Pat. No. 5,512,190 and the dialkyl dithiocarbamate-derived organic ethers of U.S. Patent No. 5,514,189.

U.S. Pat. No. 5,512,190 discloses an additive that provides anti-wear properties to a lubricating oil. The additive is the reaction product of 2,5-dimercapto-1,3,4-thiadiazole and a mixture of unsaturated mono-, di-, and triglycerides. Also disclosed is a lubricating oil additive with anti-wear properties produced by reacting a mixture of unsaturated mono-, di-, and triglycerides with diethanolamine to provide an intermediate reaction product and reacting the intermediate reaction product with 2,5-dimercapto-1,3,4 thiadiazole.

U.S. Pat. No. 5,514,189 discloses that dialkyl dithiocarbamate-derived organic ethers have been found to be effective anti-wear/antioxidant additives for lubricants and fuels.

U.S. Pat. Nos. 5,084,195 and 5,300,243 disclose N-acyl-thiourethane thioureas as anti-wear additives specified for lubricants or hydraulic fluids.

U.S. application Ser. No. 09/872,722, filed Jun. 1, 2001, discloses a composition comprising:

(A) a lubricant, and
(B) at least one 5-alkyl-2-mercapto-1,3,4-oxadiazole compound of the formula:

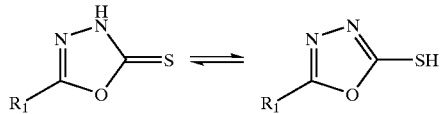

wherein $R_1$ is a hydrocarbon or functionalized hydrocarbon of from 1 to 30 carbon atoms.

The disclosures of the foregoing references are incorporated herein by reference in their entirety.

SUMMARY OF THE INVENTION

The present invention relates to compounds of the formula

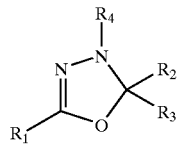

wherein $R_1$ is selected from the group consisting of hydrogen, linear or branched alkyl, alkenyl, alkaryl, aryl, alkyl ether, and alkyl ester, and $R_2$, $R_3$, and $R_4$ are independently selected from the group consisting of hydrogen, linear or branched alkyl, alkenyl, alkaryl, and aryl. The alkyl moiety can also contain within it oxygen ether, ester, and amide groups.

In the above structural formulas, $R_1$ can be a straight or branched chain, fully saturated or partially unsaturated, hydrocarbon moiety, preferably comprising alkyl or alkenyl having from 1 to 30 carbon atoms, e.g., methyl, ethyl, propyl, butyl, pentyl, hexyl, heptyl, octyl, phenyl, furfuryl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, oleenyl, nonadecenyl, eicosenyl, heneicosenyl, docosenyl, tricosenyl, tetracosenyl, pentacosenyl, triacontenyl, and the like, and isomers and mixtures thereof. Additionally, $R_1$ can be a straight or branched chain, a fully saturated or partially unsaturated hydrocarbon chain, preferably having from 1 to 30 carbon atoms, within which may be ester groups or heteroatoms, such as, oxygen and nitrogen, which may take the form of ethers, polyethers, esters, and amides.

The 1,3,4-oxadiazole compounds employed in the practice of this invention are useful as ashless, non-phosphorus-containing anti-fatigue, anti-wear, extreme pressure additives for lubricating oils. They may also provide anti-corrosion and antioxidant properties. The present invention also relates to lubricating oil compositions comprising a lubricating oil and a functional property-improving amount of at least one 1,3,4-oxadiazole compound of the above formula. More particularly, the present invention is directed to a composition comprising:

(A) a lubricant, and
(B) at least one 1,3,4-oxadiazole compound of the formula:

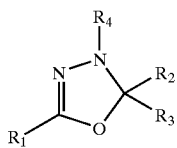

wherein
wherein $R_1$ is selected from the group consisting of hydrogen, linear or branched alkyl, alkenyl, alkaryl, aryl, alkyl ether, and alkyl ester; p2 $R_2$, $R_3$, and $R_4$ are independently selected from the group consisting of hydrogen, linear or branched alkyl, alkenyl, alkaryl, and aryl; and any alkyl moiety can optionally contain within it oxygen ether, ester, or amide groups.

It is preferred that the 1,3,4-oxadiazole is present in the compositions of the present invention in a concentration in the range of from about 0.01 to about 10 wt %.

DESCRIPTION OF THE PREFERRED EMBODIMENTS

The 1,3,4-oxadiazole compounds of the present invention are compounds of the formula:

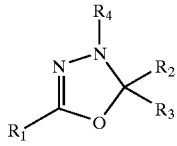

wherein
wherein $R_1$ is selected from the group consisting of hydrogen, linear or branched alkyl, alkenyl, alkaryl, aryl, alkyl ether, and alkyl ester;

$R_2$, $R_3$, and $R_4$ are independently selected from the group consisting of hydrogen, linear or branched alkyl, alkenyl, alkaryl, and aryl; and any alkyl moiety can optionally contain within it oxygen ether, ester, or amide groups.

In the above structural formula, $R_1$ is preferably an alkyl or alkenyl moiety of 1 to 30 carbon atoms, more preferably of 1 to 22 carbon atoms, most preferably of 1 to 17 carbon atoms, and can have either a straight chain or a branched chain, which can be fully saturated or partially unsaturated, e.g., methyl, ethyl, propyl, butyl, pentyl, hexyl, heptyl, octyl, nonyl, phenyl, furfuryl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, oleyl, nonadecenyl, eicosenyl, heneicosenyl, docosenyl, tricosenyl, tetracosenyl, pentacosenyl, triacontenyl, and the like, and isomers, e.g., 1-ethylpentyl, 2-ethylhexyl, and mixtures thereof Where $R_1$ is alkyl, it can be either a straight or a branched hydrocarbon chain, a fully saturated or partially unsaturated hydrocarbon chain, wherein said chains may contain ester groups or heteroatoms, such as oxygen and/or nitrogen, which may take the form of ethers, polyethers, esters, amides, and the like. As employed herein, the term "alkyl" is also intended to include "cycloalkyl." Where the alkyl is cyclic, it preferably contains from 3 to 9 carbon atoms, e.g., cyclopropyl, cyclobutyl, cyclopentyl, cyclohexyl, cycloheptyl, cyclooctyl, cyclononyl, and the like. Cycloalkyl moieties having 5 or 6 carbon atoms, i.e., cyclopentyl or cyclohexyl, are more preferred.

$R_2$, $R_3$, and $R_4$ are independently selected from the group consisting of hydrogen, linear or branched alkyl, alkenyl, alkaryl, and aryl; wherein any alkyl moiety can optionally contain within it oxygen ether, ester, or amide groups. Where any of $R_2$, $R_3$, and $R_4$ is alkyl or alkenyl, it is preferred that they be of from 1 to 30 carbon atoms, as described above. It is more preferred that $R_2$, $R_3$, and $R_4$ be selected from the group consisting of hydrogen and alkyl, e.g., lower alkyl, such as alkyl of from 1 to 4 carbon atoms.

The use of the 1,3,4-oxadiazole compounds of this invention can improve the anti-fatigue, anti-wear, and extreme pressure properties of a lubricant.

General Synthesis of Alkyl Oxadiazole Anti-wear Additives

The 5-alkyl-1,3,4-oxadiazole compounds of the present invention are prepared in a two step synthesis. The first step comprises preparing the alkyl hydrazide intermediate through the reaction of an organic acid or ester, preferably a methyl ester, with hydrazine, optionally in the presence of an inert solvent. The second synthetic step involves making the oxadiazole by reacting the alkyl hydrazide with an aldehyde or ketone, preferably formaldehyde, in an inert solvent capable of azeotroping off the water by-product. This reaction of an alkyl hydrazide with an aldehyde or ketone goes through an imine adduct intermediate between the two reactants, then cycles to the oxadiazole. It is believed that this imine adduct intermediate may also be present as a side product in the final product and may also exbibit some anti-wear properties.

Use With Other Additives

The 1,3,4-oxadiazole additives of this invention can be used as either a partial or complete replacement for the zinc dialkyldithiophosphates currently used. They can also be used in combination with other additives typically found in lubricating oils, as well as with other ashless, antiwear additives. This invention may also display synergistic effects with these other typical additives to improve oil performance properties in lubricating oils. The additives typically found in lubricating oils are, for example, dispersants, detergents, corrosion/rust inhibitors, antioxidants, antiwear agents, antifoamants, friction modifiers, seal swell agents, demulsifiers, VI improvers, pour point depressants, and the like. See, for example, U.S. Pat. No. 5,498,809 for a description of useful lubricating oil composition additives, the disclosure of which is incorporated herein by reference in its entirety. Examples of dispersants include polyisobutylene succinimides, polyisobutylene succinate esters, Mannich Base ashless dispersants, and the like. Examples of detergents include metallic alkyl phenates, metallic sulfurized alkyl phenates, metallic alkyl sulfonates, metallic alkyl salicylates, and the like. Examples of antioxidants include alkylated diphenylamines, N-alkylated phenylenediarnines, hindered phenolics, alkylated hydroquinones, hydroxylated thiodiphenyl ethers, alkylidenebisphenols, oil soluble copper compounds, and the like. Examples of anti-wear additives that can be used in combination with the additives of the present invention include organo borates, organo phosphites, organic sulfur-containing compounds, zinc dialkyldithiophosphates, zinc diaryidithiophosphates, phosphosulfuirized hydrocarbons, and the like. The following are exemplary of such additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others. Examples of friction modifiers include fatty acid esters and amides, organo molybdenum compounds, molybdenum dialkylthiocarbamates, molybdenum dialkyl dithiophosphates, tri-molybdenum cluster dialkylthiocarbamates, and the like. An example of an anti-foamant is polysiloxane, and the like. An example of a rust inhibitor is a polyoxyalkylene polyol, and the like. Examples of VI improvers include olefin copolymers and dispersant olefin copolymers, and the like. An example of a pour point depressant is polymethacrylate, and the like.

Representative conventional antiwear agents that can be used include, for example, the zinc dialkyl dithiophosphates and the zinc diaryl dithiophosphates.

Suitable phosphates include dihydrocarbyl dithiophosphates, wherein the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

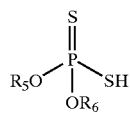

wherein $R_5$ and $R_6$ are the same or different and are alkyl, cycloalkyl, aralkyl, alkaryl or substituted substantially hydrocarbon radical derivatives of any of the above groups, and wherein the $R_5$ and $R_6$ groups in the acid each have, on average, at least 3 carbon atoms. By "substantially hydrocarbon" is meant radicals containing substituent groups (e.g., 1 to 4 substituent groups per radical moiety) such as ether, ester, nitro, or halogen that do not materially affect the hydrocarbon character of the radical.

Specific examples of suitable $R_1$ and $R_6$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl,o,p-depentylphenyl, octylphenyl, polyisobutene-(molecular weight 350)-substituted phenyl, tetrapropylene-substituted phenyl, beta-octylbutylnaphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having from about 3 to about 30 carbon atoms and aryl radicals having from about 6 to about 30 carbon atoms are preferred. Particularly preferred $R_5$ and $R_6$ radicals are alkyl of from 4 to 18 carbon atoms.

The phosphorodithioic acids are readily obtainable by the reaction of phosphorus pentasulfide and an alcohol or phenol. The reaction involves mixing, at a temperature of about 20° C. to 200° C., 4 moles of the alcohol or phenol with one mole of phosphorus pentasulfide. Hydrogen sulfide is liberated as the reaction takes place. Mixtures of alcohols, phenols, or both can be employed, e.g., mixtures of $C_3$ to $C_{30}$ alcohols, $C_6$ to $C_{30}$ aromatic alcohols, etc.

The metals useful to make the phosphate salts include Group I metals, Group II metals, aluminum, lead, tin, molybdenum, manganese, cobalt, and nickel. Zinc is the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, and nickel carbonate.

In some instances, the incorporation of certain ingredients, particularly carboxylic acids or metal carboxylates, such as, small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art and is described in a large number of issued patents, including U.S. Pat. Nos. 3,293,181; 3,397,145; 3,396,109 and 3,442,804, the disclosures of which are hereby incorporated by reference. Also useful as antiwear additives are amine derivatives of dithiophosphoric acid compounds, such as are described in U.S. Pat. No. 3,637,499, the disclosure of which is hereby incorporated by reference in its entirety.

The zinc salts are most commonly used as antiwear additives in lubricating oil in amounts of 0.1 to 10, preferably 0.2 to 2, wt. %, based upon the total weight of the lubricating oil composition. They may be prepared in accordance with known techniques by first forming a dithiophosphoric acid, usually by reaction of an alcohol or a phenol with $P_2S_5$ and then neutralizing the dithiophosphoric acid with a suitable zinc compound.

Mixtures of alcohols can be used, including mixtures of primary and secondary alcohols, secondary generally for imparting improved antiwear properties and primary for thermal stability. Mixtures of the two are particularly useful. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following formula:

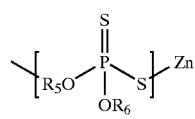

wherein $R_1$ and $R_6$ are as described in connection with the previous formula.

Especially preferred additives for use in the practice of the present invention include alkylated diphenylamines, hindered alkylated phenols, hindered alkylated phenolic esters, and molybdenum dithiocarbamates.

Lubricant Compositions

Compositions, when they contain these additives, are typically blended into the base oil in amounts such that the additives therein are effective to provide their normal attendant functions. Representative effective amounts of such additives are illustrated in TABLE 1.

TABLE 1

| Additives | Preferred Weight % | More Preferred Weight % |
| --- | --- | --- |
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 0.01–10 | 0.01–5 |
| Lube Oil Flow Improver | 0.01–2 | 0.01–1.5 |
| Detergent/Rust Inhibitor | 0.01–6 | 0.01–3 |
| Pour Point Depressant | 0.01–1.5 | 0.01–0.5 |
| Antifoaming Agent | 0.001–0.1 | 0.001–0.01 |
| Antiwear Agent | 0.001–5 | 0.001–1.5 |
| Seal Swellant | 0.1–8 | 01.–4 |
| Friction Modifier | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention, together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and/or by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil base stocks. The lubricating oil base stock is any natural or synthetic lubricating oil base stock fraction having a kinematic viscosity at 100° C. of about 2 to about 200 cSt, more preferably about 3 to about 150 cSt, and most preferably about 3 to about 100 cSt. The lubricating oil base stock can be derived from natural lubricating oils, synthetic lubricating oils, or mixtures thereof Suitable lubricating oil base stocks include base stocks obtained by isomerization of synthetic wax and wax, as well as hydrocrackate base stocks produced by hydrocracking (rather than solvent extracting) the aromatic and polar components of the crude. Natural lubricating oils include animal oils, such as, lard oil, vegetable oils (e.g., canola oils, castor oils, sunflower oils), petroleum oils, mineral oils, and oils derived from coal or shale.

Synthetic oils include hydrocarbon oils and halo-substituted hydrocarbon oils, such as, polymerized and interpolymerized olefins, alkylbenzenes, polyphenyls, alkylated diphenyl ethers, alkylated diphenyl sulfides, as well as their derivatives, analogs, homologues, and the like. Synthetic lubricating oils also include alkylene oxide polymers, interpolymers, copolymers, and derivatives thereof, wherein the terminal hydroxyl groups have been modified by esterification, etherification, etc.

Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, poly α-olefins, and the like.

The lubricating oil may be derived from unrefined, refined, rerefined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a VI of at least 130, preferably at least 135 or higher and, following dewaxing, a pour point of about −20° C. or lower.

The additives of the present invention are especially useful as components in many different lubricating oil compositions. The additives can be included in a variety of oils with lubricating viscosity, including natural and synthetic lubricating oils and mixtures thereof The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

The advantages and the important features of the present invention will be more apparent from the following examples.

EXAMPLES

Example 1

Synthesis of Oleyl Hydrazide

Into a two liter reaction flask, equipped with a mechanical stirrer, nitrogen blanket, thermocouple, and reflux condenser, is charged 862 grams of methyl oleate, 150 mL of methanol and 150 grams of hydrazine monohydrate. Under a nitrogen blanket and vigorous stirring, the reaction media are heated to 72° C. and held there for nine hours. The conversion from ester to hydrazide is easily followed by infrared analysis. The reflux condenser is replaced with a distillation head and the reaction media are placed under 100–200 mm Hg pressure (vacuum) at 80° C. to remove methanol solvent and by-product. The final product solidifies on cooling to room temperature to a soft wax consistency.

Example 2

Synthesis of 5-Heptadecenyl-1,3,4-Oxadiazole

Into a 250 mL flask, equipped with a mechanical stirrer, nitrogen blanket, Dean-Stark water trap, thermocouple, and heating mantle, is charged 29.6 grams (0.1 mole) of oleyl hydrazide and 100 mL of toluene. This mixture is then heated to 40° C. to dissolve the oleyl hydrazide in the toluene. To this stirred solution at 40° C. is slowly added 8.1 grams (0.1 mole) of 37% aqueous formaldehyde solution. After the addition is complete, the reaction media are stirred at 40° C. for 30 minutes before raising the temperature to reflux (90° C.) and holding it there for one hour. The water by-product is then allowed to be collected in the Dean-Stark water trap. When no more water is collected and the reaction media temperature reaches 120° C., the toluene solvent is stripped under vacuum, yielding 30.4 grams of product.

Example 3

Synthesis of 5-Heptyl-1,3,4-Oxadiazole

Into a 250 mL flask, equipped with a mechanical stirrer, nitrogen blanket, Dean-Stark water trap, thermocouple, and heating mantle, is charged 7.9 grams(0.05 mole) of octanoyl hydrazide and 100 mL of toluene. This mixture is then heated to 30° C. to dissolve the octanoyl hydrazide in the toluene. To this stirred solution at 30° C. is slowly added 4.05 grams (0.05 mole) of 37% aqueous formaldehyde solution. After the addition is complete, the reaction media are stirred at 30° C. for 30 minutes before raising the temperature to reflux (90° C.) and holding it there for two hours. The water by-product is than allowed to be collected in the Dean-Stark water trap. When no more water is collected and the reaction media temperature reaches 120° C., the toluene solvent is stripped under vacuum, yielding 8.7 grams of product.

Example 4

Synthesis of 5-Heptadecenyl-2,2-Dimethyl-1,3,4-Oxadiazole

Into a 250 mL flask, equipped with a mechanical stirrer, nitrogen blanket, Dean-Stark water trap, thermocouple, and heating mantle, is charged 29.6 grams (0.1 mole) of oleyl hydrazide, 0.2 gram of p-toluenesulfonic acid, and 100 mL of toluene. This mixture is then heated to 30° C. to dissolve the oleyl hydrazide in the toluene. To this stirred solution at 30° C. is slowly added 5.8 grams (0.1 mole) of acetone. After the addition is complete, the reaction media are stirred at 30° C. for 30 minutes before raising the temperature to 80° C. and holding it there for one hour. The temperature is raised to reflux and the water by-product is allowed to be collected in the Dean-Stark water trap. When no more water is collected and the reaction media temperature reaches 120° C., the toluene solvent is stripped under vacuum, yielding 32.3 grams of product.

Example 5

Synthesis of 5-Heptadecenyl-2-Furfuryl-1,3,4-Oxadiazole

Into a 250 mL flask, equipped with a mechanical stirrer, nitrogen blanket, Dean-Stark water trap, thermocouple, and heating mantle, is charged 14.8 grams (0.05 mole) of oleyl hydrazide and 75 mL of toluene. This mixture is then heated to 30° C. to dissolve the oleyl hydrazide in the toluene. To this stirred solution at 30° C. is slowly added 4.8 grams (0.05 mole) of furfuraldehyde. After the addition is complete, the reaction media are stirred at 30° C. for 30 minutes before raising the temperature to reflux (90° C.) and holding it there for one hour. The water by-product is then allowed to be collected in the Dean-Stark water trap. When no more water is collected and the reaction media temperature reaches 120° C., the toluene solvent is stripped under vacuum, yielding 22.1 grams of product.

Example 6

Four-Ball Anti-Wear Testing

The antiwear properties of the oxadiazoles of the present invention at a level of 1.0 wt % in a fully formulated SAE 5W-20 GF-3 motor oil formulation were determined in the Four-Ball Wear Test under the ASTM D 4172 test conditions. The fully formulated lubricating oils tested also contained 1 weight percent cumene hydroperoxide to help simulate the environment within a running engine. The additives were tested for effectiveness in a motor oil formulation (See description in Table 2) and compared to identical formulations with and without any zinc dialkyldithiophosphate. In Table 3, the numerical value of the test results (Average Wear Scar Diameter, mm) decreases with an increase in effectiveness.

TABLE 2

SAE 5W-20 Prototype Motor Oil Formulations

| Component | Formulation A (wt %) |
| --- | --- |
| Solvent Neutral 100 | 22.8 |
| Solvent Neutral 150 | 60 |
| Succinimide Dispersant | 7.5 |
| Overbased Calcium Phenate Detergent | 2.0 |
| Neutral Calcium Sulfonate Detergent | 0.5 |
| Rust Inhibitor | 0.1 |
| Antioxidant | 0.5 |
| Pour Point Depressant | 0.1 |
| OCP VI Improver | 5.5 |
| Anti-wear Additive[1] | 1.0 |

[1]In the case of No anti-wear additive in Table 2, solvent neutral 100 is put in its place at 1.0 weight percent.

TABLE 3

Four-Ball Wear Results

| Compound | Formulation | Wear Scar Diameter, mm |
| --- | --- | --- |
| No antiwear additive | A | 0.73 (0.74)* |
| 1.0 weight % Zinc dialkyldithiophosphate | A | 0.50 (0.51) |
| 0.5 weight % Zinc dialkyldithiophosphate | A | 0.70 (0.67) |
| 5-heptadecenyl-1,3,4-oxadiazole | A | 0.38 (0.38) |
| 5-heptyl-1,3,4-oxadiazole | A | 0.54 (0.56) |
| 5-heptadecenyl-2,2-dimethyl-1,3,4-oxadiazole | A | 0.70 |
| 5-heptadecenyl-2-furfuryl-1,3,4-oxadiazole | A | 0.38 (0.39) |

*Numbers in parentheses are repeat test results.

Example 7

Cameron-Plint TE77 High Frequency Friction Machine Anti-wear Testing

Another test used to determine the anti-wear properties of these products is the Cameron-Plint Anti-wear test based on a sliding ball on a plate. The specimen parts (6 mm diameter AISI 52100 steel ball of 800±20 kg/mm$^2$ hardness and hardened ground NSOH B01 gauge plate of RC 60/0.4 micron) are rinsed and then sonicated for 15 minutes with technical grade hexanes. This procedure is repeated with isopropyl alcohol. The specimens are dried with nitrogen and set into the TE77. The oil bath is filled with 10 mL of sample. The test is run at a 30 Hertz Frequency, 100 Newton Load, 2.35 mm Amplitude. The test starts with the specimens and oil at room temperature. Immediately, the temperature is ramped over 15 minutes to 50° C., where it dwells for 15 minutes. The temperature is then ramped over 15 minutes to 100° C., where it dwells for 45 minutes. A third temperature ramp over 15 minutes to 150° C. is followed by a final dwell at 150° C. for 15 minutes. The total length of the test is 2 hours. At the end of the test, the wear scar diameter on the 6 mm ball is measured using a Leica StereoZoom® Stereomicroscope and a Mitutoyo 164 series Digimatic Head.

In the Examples below, the fully formulated lubricating oils tested contained 1 wt. % cumene hydroperoxide to help simulate the environment within a running engine. The test additive was blended at 1.0 wt. % in a fully formulated SAE 5W-20 Prototype GF-4 Motor Oil formulation containing no ZDDP. The additives were tested for effectiveness in this motor oil formulation (See description in Table 4) and compared to identical formulations with and without any zinc dialkyldithiophosphate. In Table 4 the numerical value of the test results (Ball Wear Scar Diameter, Plate Scar Width, and Plate Scar Depth) decreases with an increase in effectiveness.

TABLE 4

Cameron-Plint Wear Test

| Additive at 1.0 Weight Percent | Ball Scar (mm) | Plate Scar Width (mm) | Plate Scar Depth (μm) |
| --- | --- | --- | --- |
| 5-Heptadecenyl-1,3,4-oxadiazole | 0.55 (0.61)* | 0.71 (0.83) | 7.86 (8.94) |
| No anti-wear additive[1] | 0.66 | 0.74 | 15.05 |
| Zinc dialkyldithiophosphate (1.0 wt %) | 0.39 | 0.72 | 1.83 |
| Zinc dialkyldithiophosphate (0.5 wt %) | 0.62 | 0.76 | 14.77 |

*Numbers in parentheses are repeat test results.
[1]In the case of No anti-wear additive in Table 4, solvent neutral 100 is put in its place at 1.0 weight percent.

In view of the many changes and modifications that can be made without departing from principles underlying the invention, reference should be made to the appended claims for an understanding of the scope of the protection to be afforded the invention.

What is claimed is:

1. A composition comprising:
   (A) a lubricant, and
   (B) at least one 1,3,4-oxadiazole compound of the formula:

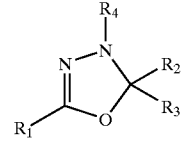

wherein $R_1$ is selected from the group consisting of hydrogen, linear or branched alkyl, alkenyl, alkaryl, aryl, alkyl ether, and alkyl ester;

$R_2$, $R_3$, and $R_4$ are independently selected from the group consisting of hydrogen, linear or branched alkyl, alkenyl, alkaryl, and aryl; and any alkyl moiety can optionally contain within it oxygen ether, ester, or amide groups.

2. The composition of claim 1 wherein the lubricant is a lubricating oil.

3. The composition of claim 1 wherein $R_1$ is an alkyl or alkenyl moiety of from 1 to 30 carbon atoms.

4. The composition of claim 2 wherein $R_1$ is an alkyl or alkenyl moiety of from 1 to 30 carbon atoms.

5. The composition of claim 1 wherein $R_1$ is an alkyl chain of from 1 to 22 carbon atoms.

6. The composition of claim 2 wherein $R_1$ is an alkyl chain of from 1 to 22 carbon atoms.

7. The composition of claim 1 wherein $R_1$ is an alkenyl chain of from 1 to 22 carbon atoms.

8. The composition of claim 2 wherein $R_1$ is an alkenyl chain of from 1 to 22 carbon atoms.

9. The composition of claim 1 wherein $R_1$ is a hydrocarbon chain of from 1 to 30 linear carbon atoms containing at least one member selected from the group consisting of ether oxygen, ester, and amide within the chain.

10. The composition of claim 2 wherein $R_1$ is a hydrocarbon chain of from 1 to 30 linear carbon atoms containing at least one member selected from the group consisting of ether oxygen, ester, and amide within the chain.

11. The composition of claim 1 wherein the 1,3,4-oxadiazole is a 5-alkyl-1,3,4-oxadiazole and is present in a concentration in the range of from about 0.01 to about 10 wt %.

12. The composition of claim 2 wherein the 1,3,4-oxadiazole is a 5-alkyl-1,3,4-oxadiazole and is present in a concentration in the range of from about 0.01 to about 10 wt %.

13. The composition of claim 1 wherein $R_2$, $R_3$, and $R_4$ are independently selected from the group consisting of hydrogen, aryl, and alkyl.

14. The composition of claim 2 wherein $R_2$, $R_3$, and $R_4$ are independently selected from the group consisting of hydrogen, aryl, and alkyl.

15. The composition of claim 1 further comprising at least one additive selected from the group consisting of dispersants, detergents, corrosion/rust inhibitors, zinc dialkyldithiophosphates, VI improvers, pour point depressants, antioxidants, and friction modifiers.

16. The composition of claim 2 further comprising at least one additive selected from the group consisting of dispersants, detergents, corrosion/rust inhibitors, zinc dialkyldithiophosphates, VI improvers, pour point depressants, antioxidants, and friction modifiers.

17. The composition of claim 1 further comprising at least one member selected from the group consisting of zinc dialkyldithiophosphates, zinc diaryldithiophosphates, and mixtures thereof.

18. The composition of claim 2 further comprising at least one member selected from the group consisting of zinc dialkyldithiophosphates, zinc diaryldithiophosphates, and mixtures thereof.

19. The composition of claim 1 further comprising at least one additive selected from the group consisting of alkylated diphenylamines, hindered alkylated phenols, hindered alkylated phenolic esters, and molybdenum dithiocarbamates.

20. The composition of claim 2 further comprising at least one additive selected from the group consisting of alkylated diphenylamines, hindered alkylated phenols, hindered alkylated phenolic esters, and molybdenum dithiocarbamates.

* * * * *